United States Patent
Choi et al.

(10) Patent No.: US 10,428,007 B2
(45) Date of Patent: Oct. 1, 2019

(54) METHOD FOR PRODUCING UNSATURATED ALDEHYDE AND UNSATURATED CARBOXYLIC ACID

(71) Applicant: LG CHEM, LTD., Seoul (KR)

(72) Inventors: Byung Yul Choi, Daejeon (KR); Hyun Jong Shin, Daejeon (KR); Junghoon Chang, Daejeon (KR); Young Hyun Choe, Daejeon (KR); Jun Seok Ko, Daejeon (KR); Sang Hun Jeon, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/082,704

(22) PCT Filed: Oct. 17, 2017

(86) PCT No.: PCT/KR2017/011476
§ 371 (c)(1),
(2) Date: Sep. 6, 2018

(87) PCT Pub. No.: WO2018/084460
PCT Pub. Date: May 11, 2018

(65) Prior Publication Data
US 2019/0092713 A1  Mar. 28, 2019

(30) Foreign Application Priority Data
Nov. 1, 2016  (KR) .................. 10-2016-0144601

(51) Int. Cl.
| | |
|---|---|
| *C07C 45/35* | (2006.01) |
| *C07C 51/00* | (2006.01) |
| *B01J 23/00* | (2006.01) |
| *C07C 51/25* | (2006.01) |
| *B01J 8/06* | (2006.01) |
| *B01J 23/887* | (2006.01) |
| *B01J 37/02* | (2006.01) |
| *B01J 37/03* | (2006.01) |
| *B01J 37/04* | (2006.01) |
| *B01J 37/08* | (2006.01) |

(52) U.S. Cl.
CPC ............. *C07C 51/252* (2013.01); *B01J 8/067* (2013.01); *B01J 23/8876* (2013.01); *B01J 37/0236* (2013.01); *B01J 37/038* (2013.01); *B01J 37/04* (2013.01); *B01J 37/08* (2013.01); *C07C 45/35* (2013.01); *B01J 2208/0053* (2013.01); *B01J 2208/00212* (2013.01); *B01J 2208/00221* (2013.01); *B01J 2208/00238* (2013.01); *B01J 2208/00849* (2013.01); *B01J 2208/021* (2013.01); *B01J 2208/025* (2013.01); *B01J 2208/065* (2013.01); *B01J 2523/00* (2013.01)

(58) Field of Classification Search
CPC ..... C07C 45/35; C07C 51/252; B01J 23/8876
See application file for complete search history.

(56) References Cited

U.S. PATENT DOCUMENTS

| | | | |
|---|---|---|---|
| 5,198,581 A | 3/1993 | Kawajiri et al. | |
| 6,028,220 A | 2/2000 | Wada et al. | |
| 6,399,818 B2 | 6/2002 | Tanimoto et al. | |
| 6,781,013 B2 | 8/2004 | Tanimoto | |
| 6,888,024 B2 | 5/2005 | Dieterle et al. | |
| 6,960,684 B2 | 11/2005 | Yunoki | |
| 7,238,836 B2 * | 7/2007 | Ha ........................ | C07C 51/252 422/652 |
| 7,868,202 B2 | 1/2011 | Yada et al. | |
| 2002/0007088 A1 | 1/2002 | Tanimoto et al. | |
| 2004/0249000 A1 | 12/2004 | Yada et al. | |
| 2005/0049435 A1 | 3/2005 | Ha et al. | |
| 2006/0211885 A1 | 9/2006 | Yoo et al. | |
| 2010/0036157 A1 | 2/2010 | Ko et al. | |
| 2016/0145181 A1 | 5/2016 | Nakazawa et al. | |

FOREIGN PATENT DOCUMENTS

| | | |
|---|---|---|
| EP | 1097745 A1 | 5/2001 |
| EP | 1484299 A1 | 12/2004 |
| GB | 2001257 A | 1/1979 |
| JP | 2001-328951 A | 11/2001 |
| JP | 2005-187460 A | 7/2005 |
| JP | 3939187 B2 | 7/2007 |
| JP | 3943311 B2 | 7/2007 |
| KR | 10-2005-0024206 A | 3/2005 |
| KR | 10-2006-0094874 A | 8/2006 |
| KR | 10-2012-0079617 A | 7/2012 |
| KR | 10-1257411 B1 | 4/2013 |
| KR | 10-2016-0032037 A | 3/2016 |
| WO | 2005-049536 A1 | 6/2005 |
| WO | 2007-097573 A1 | 8/2007 |

* cited by examiner

*Primary Examiner* — Sikarl A Witherspoon
(74) *Attorney, Agent, or Firm* — Dentons US LLP

(57) ABSTRACT

The present invention relates to a method for producing unsaturated aldehydes and unsaturated carboxylic acids. According to the present invention, a method for producing unsaturated aldehydes and unsaturated carboxylic acids which can impart activity and control temperature independently in fixed catalyst layer zones in a shell-and-tube reactor, thereby exhibiting improved yield and operation stability, is provided.

7 Claims, No Drawings

METHOD FOR PRODUCING UNSATURATED ALDEHYDE AND UNSATURATED CARBOXYLIC ACID

CROSS-REFERENCE TO RELATED APPLICATION(S)

This application is a National Stage of International Application No. PCT/KR2017/011476 filed on Oct. 17, 2017, and claims the benefit of Korean Application No. 10-2016-0144601 filed on Nov. 1, 2016, all of which are hereby incorporated by reference in their entirety for all purposes as if fully set forth herein.

TECHNICAL FIELD

The present invention relates to a method for producing unsaturated aldehydes and unsaturated carboxylic acids.

BACKGROUND ART

In general, a multi-tubular shell-and-tube reactor in the form of a heat exchanger is a type of reactor that is used for the purpose of efficiently removing heat produced in a reaction. Such a reactor has a solid catalyst filled in a plurality of reaction tubes, and supplies a raw material gas into the reaction tubes to create a chemical reaction in order to obtain a desired component. In addition, a heat medium circulates through a reactor shell so that the chemical reaction can take place in an optimum condition.

The multi-tubular shell-and-tube reactor tends to have hot spots at specific areas of the reaction tubes. Such hot spots cause problems such as of shortened lifetime and degraded selectivity for a desired target product owing to the deterioration of the catalyst.

Thus, various approaches have been promoted to achieve efficient heat transfer to the plurality of the reaction tubes inside the reactor in order to decrease the hot spots. However, in a high-load reaction process, the degree of improvement due to these approaches is not sufficient, and therefore a need to develop a technology capable of securing high yield and operation stability while effectively controlling the temperature of the hot spots still remains.

PRIOR ART LITERATURE

Patent Literature (Patent Literature 1) Korean Patent Laid-open Publication No. 2006-0094874 (Aug. 30, 2006)
(Patent Literature 2) Korean Patent Laid-open Publication No. 2012-0079617 (Jul. 13, 2012)

DETAILED DESCRIPTION OF THE INVENTION

Technical Problem

It is one object of the present invention to provide a method for producing unsaturated aldehydes and unsaturated carboxylic acids which effectively controls the heat of reaction to exhibit improved yield and operation stability.

Technical Solution

According to the present invention, there is provided a method for producing unsaturated aldehydes and unsaturated carboxylic acids corresponding to a raw material in which at least one compound selected from propylene, isobutylene, t-butyl alcohol, and methyl-t-butyl ether is added as the raw material and subjected to gas phase contact oxidation with molecular oxygen or a molecular oxygen-containing gas, using a fixed-bed multistage heat medium circulating type of multi-tubular shell-and-tube reactor filled with a catalyst, wherein the multistage heat medium circulating type of multi-tubular shell-and-tube reactor includes a cylindrical shell, a plurality of tube sheets for separating the inside of the shell into a plurality of independent spaces, a baffle for dividing the plurality of independent spaces inside the shell into two spatially continuous zones, and a plurality of reaction tubes fixed to the inside of the shell while penetrating through the plurality of tube sheets and the baffle, wherein in the plurality of independent spaces inside the shell, the heat transfer to the reaction tube is performed independently at a temperature of 280 to 400° C. by the flow of an independent heat medium, and wherein at least four spatially continuous fixed catalyst layer zones exist in the reaction tube, and the fixed catalyst layer zones have high activity in the direction from an inlet to an outlet of the reaction tube.

Hereinafter, a method for producing unsaturated aldehydes and unsaturated carboxylic acids according to a specific embodiment of the present invention will be described in detail.

First, unless explicitly stated otherwise, the terminology used herein is for the purpose of describing particular embodiments only and is not intended to limit the scope of the invention.

The singular forms used herein are intended to include the plural forms as well, unless the context clearly indicates to the contrary.

It will be further understood that the meaning of the terms "comprise" and "include" as used herein is intended to specify the presence of stated features, ranges, integers, steps, operations, elements, and/or components, but does not preclude the presence or addition of other features, ranges, integers, steps, operations, elements, components, and/or groups.

The present inventors conducted intensive studies and found that in the method for producing unsaturated aldehydes and unsaturated carboxylic acids using a fixed-bed multi-tubular shell-and-tube reactor, when heat transfer to the reaction tubes is performed at independent temperatures through independent multistage heat medium circulation and a fixed catalyst layer zone having high activity is introduced in the direction from an inlet to an outlet of the reaction tube, improved yield and operational stability can be secured.

When the raw material gas flows into the reaction tube, the concentration of the reactant is high at the front stage of the reaction tube, and thus heat generation becomes locally severe, but the process for producing unsaturated aldehydes and unsaturated carboxylic acids according to the present invention can impart activity and control temperature independently for the fixed catalyst layer zones in the shell-and-tube reactor, thereby exhibiting improved yield and operation stability.

Specifically, according to one embodiment of the present invention, there is provided a method for producing unsaturated aldehydes and unsaturated carboxylic acids corresponding to a raw material in which at least one compound selected from propylene, isobutylene, t-butyl alcohol, and methyl-t-butyl ether is added as the raw material and subjected to gas phase contact oxidation with molecular oxygen or a molecular oxygen-containing gas, using a fixed-bed multistage heat medium circulating type of multi-tubular shell-and-tube reactor filled with a catalyst, wherein the multistage heat medium circulating type of multi-tubular shell-and-tube reactor includes a cylindrical shell, a plurality of tube sheets for separating the inside of the shell into a plurality of independent spaces, a baffle for dividing the plurality of independent spaces inside the shell into two spatially continuous zones, and a plurality of reaction tubes fixed to the inside of the shell while penetrating through the plurality of tube sheets and the baffle, wherein in the plurality of independent spaces inside the shell, the heat transfer to the reaction tube is performed independently at a temperature of 280 to 400° C. by the flow of independent heat medium, and wherein at least four spatially continuous fixed catalyst layer zones exist in the reaction tube, and the fixed catalyst layer zones have high activity in the direction from an inlet to an outlet of the reaction tube.

According to one embodiment of the present invention, the method for producing unsaturated aldehydes and unsaturated carboxylic acids is performed by using a cylindrical shell, a plurality of tube sheets for separating the inside of the shell into a plurality of independent spaces, and a baffle for dividing the plurality of independent spaces inside the shell into two spatially continuous zones, and a plurality of reaction tubes fixed to the inside of the shell while penetrating through the plurality of tube sheets and the baffle.

The inside of the shell is separated into a plurality of independent spaces by the plurality of tube sheets, and in the plurality of spaces, heat transfer to the reaction tube is performed independently at a temperature of 280 to 400° C. by the flow of an independent heat medium.

Preferably, in the plurality of independent spaces inside the shell, heat transfer to the reaction tube is performed by the flow of an independent multi-stage heat medium having a high temperature in the direction from an inlet to an outlet of the reaction tube.

At least four spatially continuous fixed catalyst layer zones exist in the reaction tube, and the fixed catalyst layer zone is filled with a catalyst so as to have high activity in the direction from an inlet to an outlet of the reaction tube.

The tube sheet separates the inner space of the shell to enable adjustment of the reaction temperature by an independent heat medium. A plurality of independent spaces inside the shell are provided with an annular conduit that is connected to the heat medium supply duct and an annular conduit connected to the exhaust duct, thereby enabling the flow of each independent heat medium.

In the flow of each independent heat medium, the heat medium that is supplied through the annular conduit connected to the supply duct is heat-exchanged with the reaction tube while flowing along an S-shaped flow path formed by the baffle.

The raw material gas is supplied through a supply duct connected to a plurality of reaction tubes. After being reacted while passing through the plurality of reaction tubes, the reactant is collected again and discharged through an outlet duct.

As the heat medium, a molten salt containing a nitrate and/or a nitrite can be used.

Hereinafter, a case where the inside of the shell is spatially separated into two independent spaces will be described as a representative example. However, this is presented as one embodiment according to the present invention, and it is not intended to limit the scope of the present invention, and various modifications may be made without departing from the scope of the present invention.

As a representative example, in a shell-and-tube reactor in which the production method of unsaturated aldehydes and unsaturated carboxylic acids is carried out, the plurality of the tube sheets separate the inside of the shell into two independent spaces, two spaces separated by the plurality of tube sheets are divided into two spatially continuous zones by a baffle, and four fixed catalyst layer zones corresponding to the zones formed by the baffle may exist in the reaction tube.

Specifically, the fixed catalyst layer zone includes the first to fourth fixed catalyst layer zones having high activity in the direction from an inlet to an outlet of the reaction tube, and the first fixed catalyst layer zone can have activity which is 75 to 85% of the catalytic activity of the fourth fixed catalyst layer zone.

Preferably, when the first fixed catalyst layer zone exhibits activity which is 75 to 85% of the catalytic activity of the fourth fixed catalyst layer zone, the second fixed catalyst layer zone exhibits activity which is 85 to 95% of the catalytic activity of the fourth fixed catalyst layer zone, and the third fixed catalyst layer zone exhibits activity which is 95 to 98% of the catalytic activity of the fourth fixed catalyst layer zone, it can be advantageous in securing improved yield and operation stability.

The inside of the shell is separated into first and second independent inner spaces in the direction from an inlet to an outlet of the reaction tube by the plurality of tube sheets, and the temperature of the first heat medium flowing through the first inner space may be adjusted to be lower than the temperature of the second heat medium flowing through the second inner space.

Preferably, in the first inner space, heat transfer to the reaction tube is performed at a temperature of 295 to 350° C. by the flow of the first heat medium, and in the second inner space, heat transfer to the reaction tube is performed at a temperature of 300 to 400° C. by the flow of the second heat medium.

As described above, heat transfer to the reaction tube is performed at independent temperatures through independent multistage heat medium circulation, and a fixed catalyst layer zone having high activity in the direction from an inlet to an outlet of the reaction tube is introduced, thereby securing a high yield and operation stability while effectively controlling the temperature of the hot spot.

On the other hand, the catalytic activity of the fixed catalyst layer zone can be controlled by adjusting the size of the catalyst to be filled, the volume occupied by the catalyst, the type of the alkali metal, the content ratio of the alkali metal, the calcination temperature, and the like.

The catalyst may be a composite metal oxide represented by the following Chemical Formula 1.

$$Mo_aBi_bM^1_cM^2_dM^3_eM^4_fM^5_gM^6_hO_i \qquad \text{[Chemical Formula 1]}$$

In Chemical Formula 1,

Mo is molybdenum,

Bi is bismuth, $M^1$ is at least one element selected from the group consisting of W, Sb, As, P, Sn, and Pb, $M^2$ is at least one element selected from the group consisting of Fe, Zn, Cr, Mn, Cu, Pd, Ag, and Ru, $M^3$ is at least one element selected from the group consisting of Co, Cd, Ta, Pt, and Ni, $M^4$ is at least one element selected from the group consisting of Al, Zr, V, and Ce, $M^5$ is at least one element selected from the group consisting of Se, Ga, Ti, Ge, Rh, and Au, $M^6$ is at least one element selected from the group consisting of Na, K, Li, Rb, Cs, Ca, Mg, Sr, and Ba, and a, b, c, d, e, f, g, h, and i are an atomic ratios of respective elements, wherein a=12, b is in a range of 0.01 to 20, c is in a range of 0 to 20, d is in a range of 0.001 to 15, e is in a range of 0.001 to 20, f is in a range of 0 to 20, g is in a range of 0 to 10, h is in a range of 0.001 to 10, and i is a numerical value that is determined by the state of oxidation of the respective elements.

The raw material compound used for forming the catalyst is not particularly limited, and ammonium salts, nitrates, carbonates, chlorides, sulfates, hydroxides, organic acid salts, oxides, or mixtures thereof of the metal elements can be applied in combination.

The catalyst can be produced by a method comprising the steps of preparing a suspension in which the above-mentioned raw material compound is dissolved or dispersed in water, drying the suspension to obtain a solid material, molding the solid material into a suitable shape, and calcining the molded solid material.

Further, the catalyst may be supported on an inert carrier before use. In the case of using the inert carrier, before carrying out the drying step, a step of bringing the suspension into contact with an inert carrier and supporting it can be additionally carried out.

The shape of the catalyst is not particularly limited, and a spherical shape, a columnar shape (cylindrical shape), a hollow cylindrical type, a ring shape, an irregular shape, and so on can be applied. The shape of the catalyst filled in the fixed catalyst layer zone can be the same or different (for example, the inlet side of the reaction tube has a spherical catalyst, the outlet side of the reaction tube has a pellet shaped catalyst, etc.). However, in general, it is desirable to fill a catalyst of the same shape.

With respect to the size of the catalyst, in the case of a columnar shape, the ratio (L/D) of the length (L) and the outer diameter (D) of the catalyst is preferably in a range of 0.5 to 1.3, and in the case of columnar and spherical shapes, the outer diameter D of the catalyst is preferably in a range of 3 to 10 mm.

The calcination may be performed at a temperature of 300 to 600° C. for 1 to 10 hours under air flow of 0.2 to 2 m/s. The calcination can be performed under an inert gas atmosphere, an oxidizing atmosphere, or a reducing atmosphere.

According to an embodiment of the present invention, the reaction conditions of the gas phase contact oxidation can be applied under ordinary conditions in the process for producing unsaturated aldehydes and unsaturated carboxylic acids corresponding to raw materials in which at least one compound selected from propylene, isobutylene, t-butyl alcohol, and methyl-t-butyl ether is added as a raw material and subjected to gas phase contact oxidation with molecular oxygen or a molecular oxygen-containing gas.

As an example, the intended reaction can be carried out by bringing a gaseous mixture containing propylene with a space velocity of 90 hr$^{-1}$ or more, 10 to 20% by volume of molecular oxygen, and an inert gas (e.g., nitrogen, carbon dioxide, water vapor, etc.) acting as 60 to 80% by volume of a diluent, into contact with a catalyst at a temperature of 250 to 500° C., a pressure of 0.1 to 3 kg/cm$^2$, and a space velocity of 300 to 5000 hr$^{-1}$ (STP) for the total flow rate.

Further, the analysis of reactants and products can be carried out through gas chromatography.

Advantageous Effects

According to the present invention, a method for producing unsaturated aldehydes and unsaturated carboxylic acids which can impart activity and control temperature independently for a fixed catalyst layer zone of a shell-and-tube reactor, thereby exhibiting improved yield and operation stability, is provided.

DETAILED DESCRIPTION OF THE EMBODIMENTS

Preferred embodiments will be provided below in order to assist in the understanding of the present disclosure. However, these examples are provided for the purpose of illustration only, and are not intended to limit the scope of the present invention thereto in any way.

Preparation Example 1

While 2500 ml of distilled water was heated and stirred at 70 to 85° C., 1000 g of ammonium molybdate was dissolved therein to prepare a solution (1).

274 g of bismuth nitrate, 228 g of iron nitrate, and 4.7 g of potassium nitrate were added to 400 ml of distilled water, and were well mixed with each other, then 71 g of nitric acid was added thereto and dissolved therein to prepare a solution (2).

1097 g of cobalt nitrate was dissolved in 200 ml of distilled water to prepare a solution (3).

After the solution (2) and the solution (3) were mixed with each other, while the temperature of the solution was maintained at 40 to 60° C., they were mixed with the solution (1) to prepare a catalyst suspension.

The prepared catalyst suspension was dried to obtain a catalyst solid content, which was pulverized to a particle size of 150 μm or less.

The pulverized catalyst powder was mixed for 2 hours and then molded into a cylindrical shape having an outer diameter (D) of 7.0 mm and a length (L) of 7.7 mm.

The cylindrical catalyst was calcined at 480° C. for 5 hours under an air atmosphere to obtain a composite metal oxide catalyst (catalyst A) of $M_{12}B_{1.2}Fe_{1.2}Co_{8.0}K_{0.1}$.

Preparation Example 2

A composite metal oxide catalyst (catalyst B) of $M_{12}B_{1.2}Fe_{1.2}Co_{8.0}K_{0.08}$ was obtained in the same manner as in Preparation Example 1, except that the content of potassium nitrate was adjusted to 3.76 g, the catalyst powder was molded into a cylindrical shape having an outer diameter (D) of 6.0 mm and a length (L) of 6.5 mm, and it was calcined at 470° C. for 5 hours in an air atmosphere.

Preparation Example 3

A composite metal oxide catalyst (catalyst C) of $M_{12}B_{1.2}Fe_{1.2}Co_{8.0}K_{0.06}$ was obtained in the same manner as in Preparation Example 1, except that the content of potassium nitrate was adjusted to 2.82 g, the catalyst powder was molded into a cylindrical shape having an outer diameter (D) of 5.0 mm and a length (L) of 5.5 mm, and it was calcined at 460° C. for 5 hours in an air atmosphere.

Preparation Example 4

A composite metal oxide catalyst (catalyst D) of $M_{12}B_{1.2}Fe_{1.2}Co_{8.0}K_{0.05}$ was obtained in the same manner as in Preparation Example 1, except that the content of potassium nitrate was adjusted to 2.35 g, the catalyst powder was molded into a cylindrical shape having an outer diameter (D) of 4.0 mm and a length (L) of 4.5 mm, and it was calcined at 450° C. for 5 hours in an air atmosphere.

Example 1

A shell-and-tube reactor including a cylindrical shell, three tube sheets for separating the inside of the shell into two independent spaces, a baffle for dividing two independent spaces inside the shell into two spatially continuous zones, and a plurality of reaction tubes (inner diameter 1 inch, length 300 cm, stainless steel) fixed to the inside of the shell while penetrating through the tube sheets and the baffle was prepared.

In the reaction tube, the first to fourth fixed catalyst layer zones having high activity in the direction from an inlet to an outlet of the reaction tube were set as four fixed catalyst layer zones corresponding to the zones formed by the baffle.

Specifically, a first fixed catalyst layer zone filled with the catalyst A by a length of 700 mm from the inlet, a second fixed catalyst layer zone filled with the catalyst B by a length of 700 mm, a third fixed catalyst layer zone filled with the catalyst C by a length of 1000 mm, and a fourth fixed catalyst layer zone filled with the catalyst D by a length of 600 mm was set in the reaction tube.

In the first inner space on the inlet side of the reaction tube among the two independent spaces inside the shell, heat transfer to the first and second fixed catalyst layer zones in the reaction tube was performed at a temperature of 295° C. by the flow of the first heat medium (molten nitrate).

In the second inner space on the outlet side of the reaction tube among the two independent spaces inside the shell, heat transfer to the third and fourth fixed catalyst layer zones in the reaction tube was performed at a temperature of 300° C. by the flow of the second heat medium (molten nitrate) independent of the first heat medium.

A mixed gas containing propylene with a space velocity of 120 hr$^{-1}$, 16 vol % of oxygen, 10 vol % of steam, and 65 vol % of nitrogen was supplied to the reaction tube under a reaction pressure of 1 to 3 atm, and passed through at 300° C. with a contact time of 2 seconds.

Example 2

The gas phase contact oxidation reaction was performed in the same manner as in Example 1, except that a first fixed catalyst layer zone filled with the catalyst A by a length of 700 mm from the inlet, a second fixed catalyst layer zone filled with the catalyst B by a length of 700 mm, a third fixed catalyst layer zone filled with the catalyst C by a length of 800 mm, and a fourth fixed catalyst layer zone filled with the catalyst D by a length of 800 mm was set in the reaction tube.

Comparative Example 1

The gas phase contact oxidation reaction was performed in the same manner as in Example 1, except that a first fixed catalyst layer zone filled with the catalyst A by a length of 700 mm from the inlet, a second fixed catalyst layer zone filled with the catalyst B by a length of 700 mm, and a third fixed catalyst layer zone filled with the catalyst D by a length of 1600 mm was set in the reaction tube, and heat transfer to the first and second fixed catalyst layer zones was performed by the flow of the first heat medium, while heat transfer to the third fixed catalyst layer zone was performed by the flow of the second heat medium.

Comparative Example 2

The gas phase contact oxidation reaction was performed in the same manner as in Example 1, except that:

a first fixed catalyst layer zone filled with the catalyst A by a length of 700 mm from the inlet, and a second fixed catalyst layer zone filled with the catalyst by a length of 2300 mm was set in the reaction tube, and heat transfer was performed by a length of 700 mm of the first and second fixed catalyst layer zones by the flow of the first heat medium, while heat transfer to the remainder of the second fixed catalyst layer zone was performed by the flow of the second heat medium.

Test Example

In the gas phase contact oxidation reaction according to the examples and comparative examples, the temperature of a hot spot was measured, and the conversion rate (%) of propylene, the selectivity (%) for acrylic acid and acrolein, and the yield (%) were calculated according to the following mathematical equations.

Conversion rate of propylene (%)=[(molar number of reacted propylene)/(molar number of supplied propylene]*100        [Mathematical Equation 1]

Selectivity (%) for acrylic acid (AA) and acrolein (ACR)=[(molar number of produced acrylic acid and acrolein)/(molar number of reacted propylene)]*100        [Mathematical Equation 2]

Yield (%) of acrylic acid (AA) and acrolein (ACR)= [(molar number of produced acrylic acid and acrolein)/(molar number of supplied propylene)] *100        [Mathematical Equation 3]

TABLE 1

|  | Conversion rate of propylene (%) | Temperature of hot spot (° C.) | Selectivity for AA + ACR (%) | Yield of AA + ACR (%) |
|---|---|---|---|---|
| Example 1 | 98.2 | 350 | 96.55 | 94.42 |
| Example 2 | 98.4 | 353 | 96.64 | 95.10 |
| Comparative Example 1 | 98.6 | 375 | 93.40 | 92.10 |
| Comparative Example 2 | 98.7 | 377 | 93.00 | 91.80 |

Referring to Table 1, it was confirmed that in case of the production method of unsaturated aldehydes and unsaturated carboxylic acids according to the examples, not only was the temperature of the hot spot remarkably lower but also selectivity and yield of the desired product were higher, as compared with the production method of the comparative examples.

The invention claimed is:

1. A method for producing unsaturated aldehydes and unsaturated carboxylic acids corresponding to a raw material in which at least one compound selected from propylene, isobutylene, t-butyl alcohol, and methyl-t-butyl ether is added as the raw material and subjected to gas phase contact oxidation with molecular oxygen or a molecular oxygen-containing gas, using a fixed-bed multistage heat medium circulating type of multi-tubular shell-and-tube reactor filled with a catalyst,
  wherein the multistage heat medium circulating type of multi-tubular shell-and-tube reactor includes a cylindrical shell, a plurality of tube sheets for separating the inside of the shell into a plurality of independent spaces, a baffle for dividing the plurality of independent spaces inside the shell into two spatially continuous zones, and a plurality of reaction tubes fixed to the inside of the shell while penetrating through the plurality of tube sheets and the baffle,
  wherein, in the plurality of independent spaces inside the shell, heat transfer to the reaction tube is performed independently at a temperature of 280 to 400° C. by the flow of an independent heat medium,
  wherein at least four spatially continuous fixed catalyst layer zones exist in the reaction tube, the fixed catalyst layer zones have high activity in the direction from an inlet to an outlet of the reaction tube, and the fixed catalyst layer zones include first to fourth fixed catalyst layer zones, and
  wherein a length (L) and an outer diameter (D) of the catalyst decreases from the first to the fourth fixed catalyst layer zones.

2. The method for producing unsaturated aldehydes and unsaturated carboxylic acids according to claim 1, wherein, in the plurality of independent spaces inside the shell, heat transfer to the reaction tube is performed by the flow of an independent multi-stage heat medium having a high temperature in the direction from an inlet to an outlet of the reaction tube.

3. The method for producing unsaturated aldehydes and unsaturated carboxylic acids according to claim 1, wherein
  the plurality of the tube sheets separate the inside of the shell into two independent spaces,
  two spaces separated by the plurality of tube sheets are divided into two spatially continuous zones by a baffle, and
  four fixed catalyst layer zones corresponding to the zones formed by the baffle may exist in the reaction tube.

4. The method for producing unsaturated aldehydes and unsaturated carboxylic acids according to claim 3, wherein the first to fourth fixed catalyst layer zones have high activity in the direction from an inlet to an outlet of the reaction tube, and the first fixed catalyst layer zone can have activity which is 75 to 85% of the catalytic activity of the fourth fixed catalyst layer zone.

5. The method for producing unsaturated aldehydes and unsaturated carboxylic acids according to claim 3, wherein the inside of the shell is separated into first and second independent inner spaces in the direction from an inlet to an outlet of the reaction tube by the plurality of tube sheets, and the temperature of the first heat medium flowing through the first inner space is adjusted to be lower than the temperature of the second heat medium flowing through the second inner space.

6. The method for producing unsaturated aldehydes and unsaturated carboxylic acids according to claim 5, wherein in the first inner space, heat transfer to the reaction tube is performed at a temperature of 295 to 350° C. by the flow of the first heat medium, and in the second inner space, heat transfer to the reaction tube is performed at a temperature of 300 to 400° C. by the flow of the second heat medium.

7. The method for producing unsaturated aldehydes and unsaturated carboxylic acids according to claim 1, wherein the catalyst is a composite metal oxide represented by the following Chemical Formula 1, $$Mo_a Bi_b M^1_c M^2_d M^3_e M^4_f M^5_g M^6_h O_i \qquad \text{[Chemical Formula 1]}$$

In Chemical Formula 1,
Mo is molybdenum,
Bi is bismuth,
$M^1$ is at least one element selected from the group consisting of W, Sb, As, P, Sn, and Pb,
$M^2$ is at least one element selected from the group consisting of Fe, Zn, Cr, Mn, Cu, Pd, Ag, and Ru,
$M^3$ is at least one element selected from the group consisting of Co, Cd, Ta, Pt, and Ni,
$M^4$ is at least one element selected from the group consisting of Al, Zr, V, and Ce,
$M^5$ is at least one element selected from the group consisting of Se, Ga, Ti, Ge, Rh, and Au,
$M^6$ is at least one element selected from the group consisting of Na, K, Li, Rb, Cs, Ca, Mg, Sr, and Ba, and
a, b, c, d, e, f, g, h and i are an atomic ratio of respective elements,
wherein a=12, b is in a range of 0.01 to 20, c is in a range of 0 to 20, d is in a range of 0.001 to 15, e is in a range of 0.001 to 20, f is in a range of 0 to 20, g is in a range of 0 to 10, h is in a range of 0.001 to 10, and i is a numerical value that is determined by the state of oxidation of the respective elements.

* * * * *